US005968400A

United States Patent [19]
Wicks et al.

[11] Patent Number: 5,968,400
[45] Date of Patent: Oct. 19, 1999

[54] TANDEM MICROWAVE WASTE REMEDIATION AND DECONTAMINATION SYSTEM

[75] Inventors: George G. Wicks, North Aiken, S.C.; David E. Clark; Rebecca L. Schulz, both of Gainesville, Fla.

[73] Assignee: Westinghouse Savannah River Company, Aiken, S.C.; by said George G. Wicks

[21] Appl. No.: 08/911,411

[22] Filed: Aug. 14, 1997

Related U.S. Application Data

[60] Provisional application No. 60/023,406, Aug. 14, 1996.

[51] Int. Cl.⁶ ........................................................ H05B 6/64
[52] U.S. Cl. ............................................. 219/679; 219/680
[58] Field of Search ................................... 219/678, 679, 219/680, 681, 682, 686, 701, 730, 756, 757, 759; 422/21

[56] References Cited

U.S. PATENT DOCUMENTS

| | | |
|---|---|---|
| 4,940,865 | 7/1990 | Johnson et al. . |
| 5,035,858 | 7/1991 | Held et al. . |
| 5,166,488 | 11/1992 | Peppard . |
| 5,213,758 | 5/1993 | Kawashima et al. . |
| 5,270,000 | 12/1993 | Goldner et al. . |
| 5,277,868 | 1/1994 | Langford . |
| 5,322,603 | 6/1994 | Kameda et al. . |
| 5,348,235 | 9/1994 | Pappas . |
| 5,429,799 | 7/1995 | Shieh et al. . |
| 5,441,622 | 8/1995 | Langford . |
| 5,540,886 | 7/1996 | Warmbier et al. . |

OTHER PUBLICATIONS

"Microwave Technology for Waste Management Applications: Treatment of Discarded Electronic Circuitry", Wicks, G.G., Clark, D.E., and R.L. Schulz, Microwaves Theory and Applications in Materials Processing IV, D.E. Clark, W.H. Sutton and D.A. Lewis, eds., vol. 80, pp. 627–637 (1997).

"Microwave Treatment of Emissions from Waste Materials", Schulz, R.L., Folz, D.C., Clark, D.E., Schmidt, C.J., and Wicks, G.G., Microwave Processing of Materials V, M.F. Iskander, J.O. Kiggans, Jr., C., Bolomey, eds., Materials Research Society Symposium Proceedings, vol. 430, pp. 549–554 (1996).

"Microwave Technology for Waste Management Applications Including Disposition of Electronic Circuitry", Wicks, G.G., Clark, D.E., Schulz, R.L. and Folz, D.C. Microwaves: Theory & Application in Materials Processing III, Ceramic Transactions, D.E. Clark, D.C. Folz, S.J. Oda and R. Silberglitt, eds., vol. 59, pp. 79–89 (1995).

(List continued on next page.)

*Primary Examiner*—Tu Ba Hoang
*Attorney, Agent, or Firm*—Dority & Manning

[57] ABSTRACT

The invention discloses a tandem microwave system consisting of a primary chamber in which microwave energy is used for the controlled combustion of materials. A second chamber is used to further treat the off-gases from the primary chamber by passage through a susceptor matrix subjected to additional microwave energy. The direct microwave radiation and elevated temperatures provide for significant reductions in the qualitative and quantitative emissions of the treated off gases. The tandem microwave system can be utilized for disinfecting wastes, sterilizing materials, and/or modifying the form of wastes to solidify organic or inorganic materials. The simple design allows on-site treatment of waste by small volume waste generators.

17 Claims, 2 Drawing Sheets

OTHER PUBLICATIONS

"Microwave Treatment of Emissions from the Destruction of Electronic Circuity", Schulz, R.L., Folz, D.C., Clark, D.E. Schmidt, C.J. and Wicks G.G., Microwaves: Theory & Application in Materials Processing III, Ceramic Transactions, D.E. Clark, D.C. Folz, S.J. Oda and R. Silberglitt, eds., vol. 59, pp. 107–114 (1995).

"Applications of Microwave Energy for Waste Remediation", Schulz, R.L., Folz, D.C., Clark, D.E., Wicks, G.G., and Hutcheon, R.M., in Proceedings of the 28th Microwave Power Symposium of the International Microwave Power Institute Symposium, Montreal, Quebec, pp. 9–18 (1993).

"Microwave Destruction/Vitrification of Electronic Components", Schulz, R.L., Folz, D.C., Clark, D.E., and Wicks, G.G., Ceramic Transactions, Microwaves: Theory and Application in Materials Processing II, D.E. Clark, W.R. Tinga and J.R. Laia, eds., vol. 36, pp. 81–88 (1993).

"Microwave Processing of Simulated Nuclear Waste Glass II", Schulz, R.L., Folz, D.C., Clark, D.E., Hutcheon, R.M., and Wicks, G.G., Ceramic Transactions, Microwaves: Theory and Application in Materials Processing II, D.E. Clark, W.R. Tinga and J.R. Laia, eds., vol. 36, pp. 89–97 (1993).

"Microwave Processing of Simulated Nuclear Waste Glass", Schulz, R.L., Fathi, Z., Clark, D.E., and Wicks, G.G., presented at the Symposium on Microwaves: Theory and Application in Materials Processing, Apr. 28–May 2, 1991, Cinn. OH, Ceramic Transactions, Nuclear Waste Management IV, G.G. Wicks, D.F. Bickford and L.R. Bunnell, eds. vol. 23, pp. 779–786 (1991) Also published in, Microwave Processing of Materials, D.E. Clark, F.D. Gac, W.H. Sutton, eds., Ceramic Transactions, vol. 21, pp. 451–458 (1991).

TANDEM MICROWAVE WASTE REMEDIATION AND DECONTAMINATION SYSTEM

CROSS REFERENCE

This application claims the benefit of U.S. Provisional Application No. 60/023,406, filed Aug. 14, 1996, entitled "Tandem Microwave Waste Remediation System".

DISCLOSURE

The United States Government has rights in this invention pursuant to Contract No. DE-AC09-89-SR18035 between the U.S. Department of Energy and Westinghouse Savannah River Company.

BACKGROUND OF THE INVENTION

1. Field of the Invention

The invention relates to use of microwave energy to treat waste materials. The invention incorporates a dual microwave chamber system. A first chamber is used to treat the waste material housed within a crucible. As the waste is exposed to direct microwave energy and to heat, off-gas emissions from the waste material are transferred to a second chamber where additional microwave energy is used to treat the off gas emissions. It has been found that a significant qualitative and quantitative reduction in off-gas emissions can be achieved.

2. Description of Related Art

It is known in the art to use microwaves to treat waste. U.S. Pat. No. 4,940,865 to Johnson et al. provides an apparatus for the melting of materials using microwaves. U.S. Pat. No. 5,166,488 to Peppard teaches an apparatus using microwaves to melt hypodermic syringes. Johnson vents gaseous and airborne particulates outside the apparatus. Peppard uses a conventional filtering system to retain/treat off-gas emissions. Accordingly, there is room for improvement within the art of microwave processing of wastes.

SUMMARY OF THE INVENTION

It is an object of this invention to provide an apparatus and process which uses microwave radiation to physically transform a waste material.

It is a further object of this invention to provide an apparatus and a process to treat gaseous emissions with a combination of direct microwave radiation and with elevated temperatures such that the treated emissions can be discharged into the atmosphere.

It is a further and more particular object of this invention to provide a dual chamber microwave treatment apparatus and process whereby a first chamber is used to treat a solid or liquid waste material and a second chamber in communication with the first chamber is used to treat off-gases generated during the waste material microwave treatment process.

It is a further and more particular object of this invention to provide an off-gas treatment apparatus and process which uses a conventional microwave oven.

It is still a further and more particular object of this invention to provide an apparatus and process for microwave treatment of solid or liquid waste and gaseous emissions which provides for an inert gas microwaving environment.

It is still a further and more particular object of this invention to provide an apparatus and process for microwave treatment of off-gases and similar emissions in which a gas emission microwave treatment zone can provide an ion exchange medium for the capture and retention of hazardous materials which are impervious to a microwave treatment protocol.

These and other objects of the invention are accomplished by an apparatus and process that provides for a tandem hybrid microwave waste disposal system comprising: a first combustion chamber in communication with a source of microwaves; a second combustion chamber in communication with a source of microwaves, the second combustion chamber having an input region in communication with a first end of a hollow conduit, a second end of the conduit in communication with the first combustion chamber, the second combustion chamber further comprising a susceptor defining a gas-permeable matrix; an exhaust port in communication with an output region of the second combustion chamber, wherein evolved combustion off-gases from the first combustion chamber pass through the conduit into an input region of the second combustion chamber whereby the susceptor matrix is maintained at an effective temperature for further treating the off-gases, the treated off-gases exiting through the exhaust port. Such an apparatus enables a process of treating waste comprising: providing a supply of waste material within a combustion chamber; passing a fluid stream through said combustion chamber; exposing the waste material to a combination of microwave energy and radiant energy, the radiant energy supplied by a susceptor in proximity to the waste material; directing off-gases from the first combustion chamber to a second combustion chamber; radiating the off-gases in the combustion chamber with microwave energy; retaining the off-gases within the second combustion chamber until an effective amount of the off-gases are destroyed, thereby providing treated off-gases; and, venting the treated off-gases.

The invention is an improvement over prior utilizations of microwave energy because the treatment and sterilization of a heterogeneous broad range of materials is possible without extensive pretreatment. Treatment is provided for solid and liquid waste mixtures including plastics, radioactive materials, florescent tubes, rubber materials, oils, solvents, resins, volatile organic compounds and carbon filter media, etc. The microwave units are compact and portable. The second chamber provides treatment, detoxification and sterilization of off-gases emitted from the first chamber. The treated waste is a decontaminated and sterilized material, with an off-gas treated stream which requires little or no additional remediation.

DETAILED DESCRIPTION

Figure 1:
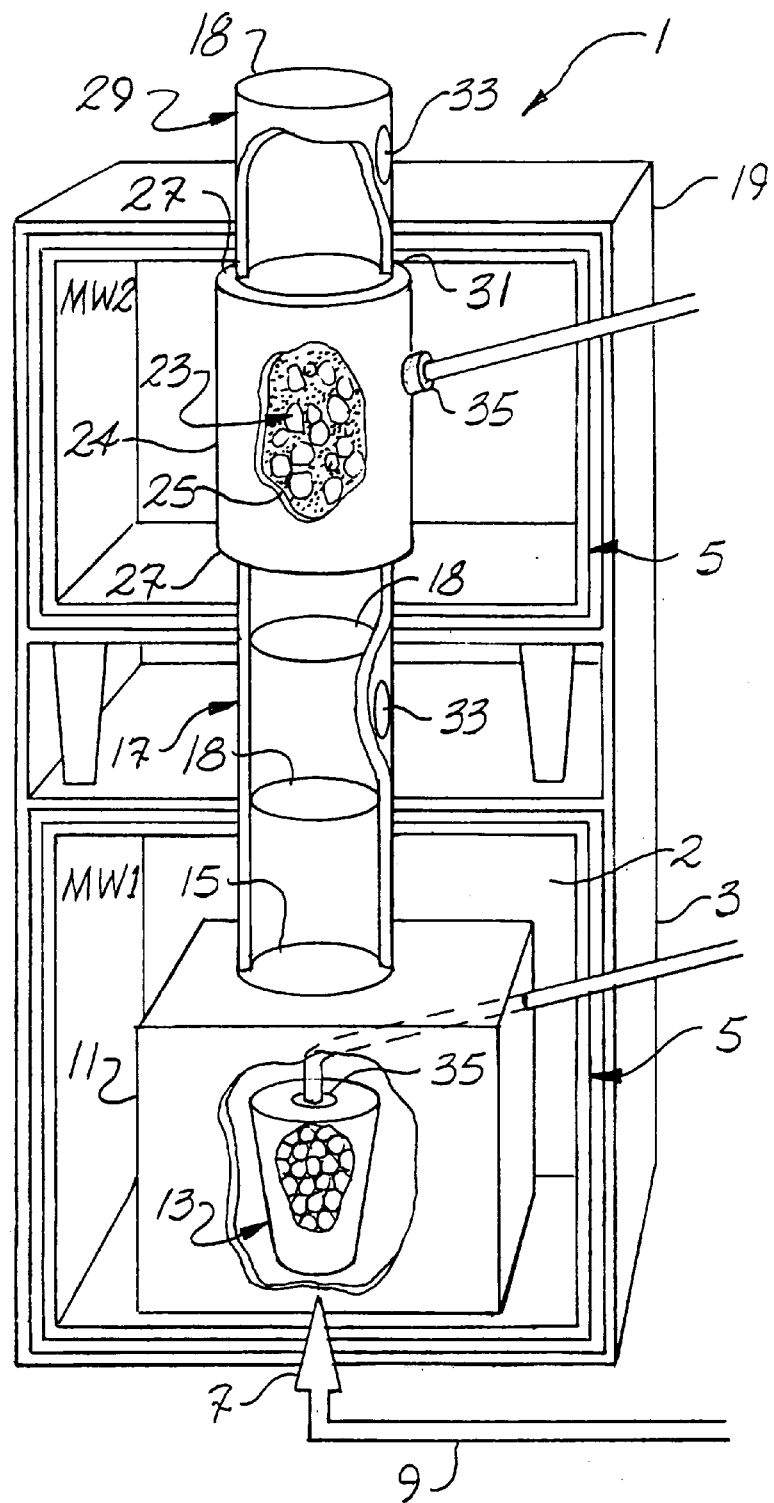
FIG. 1 depicts a schematic of a tandem microwave waste processing apparatus in accordance with this invention.

The tandem microwave waste treatment system provides for the physical and chemical alteration of waste using a two-stage treatment protocol, whereby each stage of waste treatment is carried out in a separate microwave chamber. Relevant background information can be found in the following publications which are incorporated herein by reference: Wicks, G. G., Clark, D. E., Schulz, R. L. and Roboski, R. A., "Hybrid Microwave Technology for Treatment of Hazardous Wastes, Including Electronic Circuitry with Reclamaration of Precious Metals", presented at the 1997 Global Demilitarization Symposium & Exhibition, Reno, Nev., May 5–8, 1997; Wicks, G. G., Clark, D. E., and R. L. Schulz "Microwave Technology for Waste Management Applications: Treatment of Discarded Electronic Circuitry", Microwaves Theory and Applications in Materials Processing IV, D. E. Clark, W. H. Sutton and D. A. Lewis, eds., Vol. 80, pp. 627–637 (1997); Schulz, R. L., Folz, D. C., Clark, D. E., Schmidt, C. J. and Wicks, G. G., "Microwave Waste Treatment System", presented at the First World Congress on Microwave Processing, Lake Buena Vista, Fla., Jan. 5–9, 1997; Schulz, R. L., Folz, D. C., Clark, D. E., Schmidt, C. J. and Wicks, G. G., "Microwave Treatment of Emissions from Waste Materials", Microwave Processing of Materials V, M. F. Iskander, J. O. Kiggans, Jr., C. Bolomey, eds., Materials Research Society Symposium Proceedings, Vol. 430, pp. 549–554 (1996); Wicks, G. G., Clark, D. E., Schulz, R. L. and Folz, D. C., "Microwave Technology for Waste Management Applications Including Disposition of Electronic Circuitry", Microwaves: Theory & Application in Materials Processing III, Ceramic Transactions, D. E. Clark, D. C. Folz, S. J. Oda and R. Silberglitt, eds., Vol. 59, pp. 79–89 (1995); Schulz, R. L. Folz, D. C., Clark, D. E., Wicks, G. G., and Hutcheon, R. M., "Applications of Microwave Energy for Waste Remediation", in Proceedings of the 28th Microwave Power Symposium of the International Microwave Power Institute Symposium, Montreal, Quebec, pp. 9–18 (1993); Schulz, R. L., Folz, D. C., Clark, D. E., and Wicks, G. G., "Microwave Destruction/Vitrification of Electronic Components", Ceramic Transactions, Microwaves: Theory and Application in Materials Processing II, D. E. Clark, W. R. Tinga and J. R. Laia, eds., Vol. 36, pp. 81–88 (1993); Schulz, R. L., Folz, D. C., Clark, D. E., Hutcheon, R. M. and Wicks, G. G., "Microwave Processing of Simulated Nuclear Waste Glass II", Ceramic Transactions, Microwaves: Theory and Application in Materials Processing II, D. E. Clark, W. R. Tinga and J. R. Laia, eds., Vol. 36, pp. 89–97 (1993); Schulz, R. L., Fathi, Z., Clark, D. E., and Wicks G. G., "Microwave Processing of Simulated Nuclear Waste Glass", presented at the Symposium on Microwaves: Theory and Application in Materials Processing, Apr. 28–May 2, 1991, Cinn. Ohio, Ceramic Transactions, Nuclear Waste Management IV, G. G. Wicks, D. F. Bickford and L. R. Bunnell, eds., Vol 23, pp. 779–786 (1991), also published in, Microwave Processing of Materials, D. E. Clark, F. D. Gac, W. H. Sutton, eds., Ceramic Transactions, Vol. 21, pp. 451–458 (1991).

As seen in reference to FIG. 1, a tandem microwave waste treatment apparatus 1 is illustrated. A first primary chamber 2 is defined by the interior of a 900 watt, 2.45 GHz microwave unit 3 which has been lined along interior surfaces with a refractory lining 5. An air inlet 7 has been provided along a bottom surface of the microwave unit 3. Inlet 7 is in communication through feed line 9 with a supply of compressed gas. Preferably, the compressed gas is an inert gas such as argon or nitrogen and can be introduced to the primary chamber at a controlled rate. The use of inert gases is useful to control the combustion rate and to avoid explosive operating conditions. However, it has been demonstrated that for some materials, a simple air stream will suffice.

In a preferred embodiment, a walled, covered box-like enclosure 11 of susceptor material such as SiC is placed over crucible 13 within chamber 2 of the combustion chamber, crucible 13 containing the waste material which is to be processed. An upper surface of the susceptor enclosure 11 defines an opening 15 in communication with an interconnect tube 17.

As seen in FIG. 1, interconnect tube 17 is in communication with an interior of a second microwave unit 19, positioned a spaced distance above unit 3. Similar to unit 3, a refractory lining 5 surrounds an interior 21 of microwave unit 19. A terminal end of tube 17 is interconnected to a combustion chamber 23. Filters 18 may be provided to control particulate emmissions. Combustion chamber 23 is provided by a mullite or alundum (Saint Gobain/Norton Industrial Ceramics Corp.) tube 24 partially filled within its interior with a SiC bed of 16 grit size material 25. Alternatively, chamber 23 can be filled with a plurality of stacked reticulated SiC filters as well as other appropriate susceptor materials and mixtures thereof. Chamber 23 and material 25 provide operating temperatures of between 1000–1200 degrees C. Reticulated phosphate bonded alumina (pba) filters 27 are placed at either end of chamber 23 to maintain the stability of the bed and to increase the gas emission residence time within the chamber.

An exhaust port 29 exits microwave unit 19. Port 29 is in communication at a first end with a terminal end 31 of chamber 23. Sampling ports 33 are provided on both exhaust port 29 and exhaust tube 17 to facilitate collection of gas stream samples for analyses. Thermocouples 35 are provided on both the combustion chamber 23 as well as crucible 13 to provide displayed operating temperature conditions.

In operation, the material to be treated is placed within crucible 13 of microwave unit 3. Microwave unit 19 is operated to bring the Si—C susceptor material 25 within chamber 23 to an operating temperature of between 1000–1200 degrees C. Once the operating temperature conditions are obtained, the microwave unit 3 is used to treat the material inside crucible 13 with a combination of direct microwave energy as well as indirect infrared energy which radiates from the susceptor. The microwave energy input of both units 19 and 3 can be easily controlled to achieve a desired combustion rate of the solid material as well as an effective operating temperature for the treatment of off-gases within chamber 23.

Figure 2:
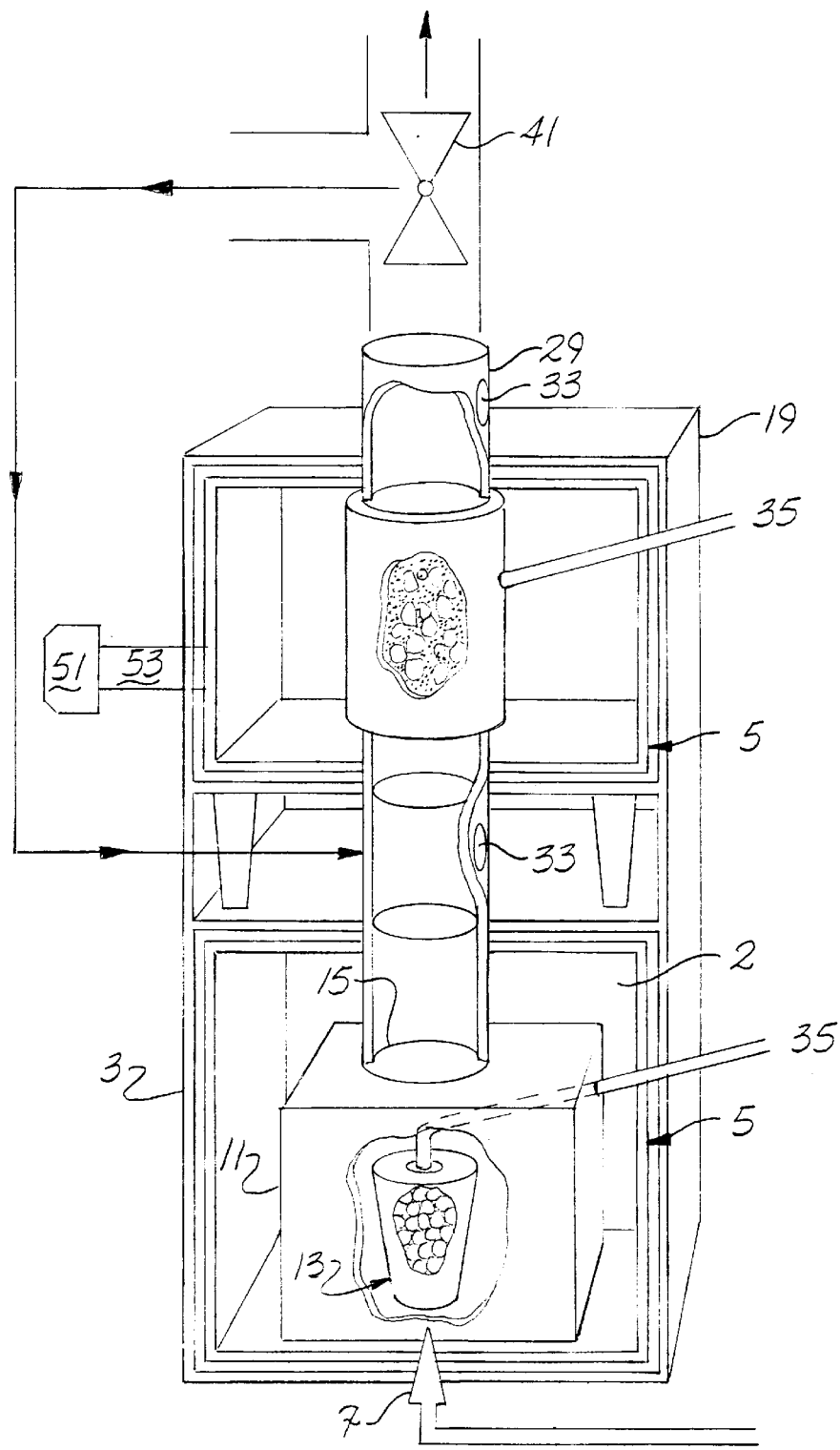
FIG. 2 depicts an alternative configuration of the microwave waste processing apparatus of this invention.

The process can be further controlled by the use of inert gases to provide a regulated fluid flow through the system. The sampling ports 33 provide the operator the ability to sample the off-gas streams following both the material waste treatment and the off-gas treatment. The present data was collected by using Tenax-TA filled glass air traps (Analytical, College Station, Tex.) which are highly absorbent for C6–C20 compounds. Following collection, the air traps were submitted for gas chromatography and mass spectrometer (GC-MS) analysis of the retained off-gases. It is envisioned that sampling ports 33 can be equipped with in-line monitors to provide real time data collection with respect to the off-gas constituents. As seen in FIG. 2, a valve 41 can be used to control the venting of treated off-gases. Should on-line monitors detect unacceptable levels of materials in the off-gas stream, the off-gas pathway can be diverted for retreatment (directional arrows) to the off-gas combustion chamber.

EXAMPLE 1

Set forth in tables 1 and 2 are the conditions and results of seven 30 minute test runs (SR-1 through SR-7) using crushed and pulverized printed electrical circuit boards as the waste material. The data was collected using a side-by-side microwave unit configuration as disclosed in the related provisional application referenced above and as discussed in Schulz, R. L., Folz, D. C., Clark, D. E., Schmidt, C. J. and Wicks, G. G., "Microwave Treatment of Emissions from Waste Materials", Microwave Processing of Materials V, M. F. Iskander, J. O. Kiggans, Jr., C. Bolomey, eds., Materials Research Society Symposium Proceedings, Vol. 430, pp.549–554 (1996).

The gaseous organic compounds that vaporize during treatment of the material in the primary chamber, were sampled at the gas sampling port 33 at the exit of the primary chamber. These values are provided in column A in Table 2. The gases were sampled following treatment in the off-gas combustion chamber and the values reported in column B of Table 2. The results demonstrate reduction of certain organic chemical off-gas concentrations to non-detectable (ND) concentrations, and reductions of other organic chemical off-gas concentrations to more than 1 order of magnitude.

TABLE 1

| Sample ID | Initial Weight (g) | Final Weight | % Wt Loss | Processing/ Off-gas Collection Time (min) | Duty Cycle* (%) |
|---|---|---|---|---|---|
| SR1 | 69.96 | 41.15 | 41.2 | 30 | 50 |
| SR2 | 70.09 | 40.66 | 41.9 | 30 | 50 |
| SR3 | 69.99 | 45.75 | 34.6 | 30 | 50 |
| SR4 | 70.05 | 41.16 | 41.2 | 30 | 100 |
| SR5 | 70.01 | 42.27 | 39.6 | 30 | 50 |
| SR6 | 70.00 | 40.85 | 41.6 | 30 | 50 |
| SR7 | 70.03 | 44.49 | 36.4 | 30 | 50 |

*Percent of time interval magnetron was activated

TABLE 2

A Summary of the GC mass Spectroscopy Results of Emissions Resulting from Combustion of Printed Circuit Boards.
(A = before microwave off-gas treatment; B = after microwave off-gas treatment)

| Compound | SR-1 (ppb) | | SR-2 (ppb) | | SR-3 (ppb) | | SR-4 (ppb) | | SR-5 (ppb) | | SR-6 (ppb) | | SR-7 (ppb) | |
|---|---|---|---|---|---|---|---|---|---|---|---|---|---|---|
| | A | B | A | B | A | B | A | B | A | B | A | B | A | B |
| Benzene* | 16.9 | 1.1 | 14.2 | nd | 19.8 | nd | 115.3 | 5.2 | 119.6 | 8.1 | 176.6 | 14.7 | 165.4 | 13.5 |
| Toluene | 28.7 | 2.7 | 24.4 | nd | 32.6 | nd | 67.5 | 6.1 | 78.7 | 6.9 | 159.1 | 18.1 | 115.7 | 5.9 |
| Ethylbenzene* | 18.7 | nd** | 19.0 | nd | 7.8 | nd | 13.9 | nd | 26.7 | nd | 142.9 | 5.0 | 91.8 | nd |
| Styrene* | 38.7 | 1.2 | 66.6 | nd | 15.0 | nd | 165.2 | 2.9 | 167.7 | 2.6 | 472.3 | 27.2 | 482.9 | 6.5 |
| Napthalane* | 1.2 | nd | 11.0 | nd | nd | nd | 75.1 | 1.3 | 35.2 | 1.3 | 6.8 | 3.4 | 47.6 | 2.4 |
| m/p Xylene* | 17.5 | nd | 1.9 | nd | nd | nd | 27.5 | nd | 23.8 | nd | 53.3 | 1.6 | 60.0 | nd |
| 1,3,5 Trimethylbenzene | 9.5 | nd | 12.4 | nd | 1.3 | nd | 15.6 | 1.6 | 18.4 | nd | 12.8 | 2.4 | 46.2 | 1.7 |
| 1,2,4 Trimethylbenzene | 17.5 | nd | 1.7 | nd | nd | nd | nd | nd | nd | nd | 15.1 | nd | 6.1 | 1.8 |

*Listed in the Clean Air Act (as amended, 1990) as hazardous air pollutants [14].
**nd = not detected (<1 ppb)

EXAMPLE 2

Set forth in Table 3 is data from two additional runs using crushed and pulverized circuit boards and following the general protocol set forth above in an upper/lower tandem microwave system as seen in FIG. 1. As set forth in Table 3, the results of the emissions analysis is set forth in nanograms. Again, significant reductions and/or elimination of certain emission waste has been obtained.

TABLE 3

Gas Chromatography Data Collected Before and After Microwave Treatment of Emissions Resulting From the Combustion of Unreinforced Circuit Boards

| COMPOUND | SR-8 EMISSIONS (ng) | | SR-9 EMISSIONS (ng) | |
|---|---|---|---|---|
| | A | B | A | B |
| Benzene* | 5838.9 | 22.2 | 1415.6 | 139.5 |
| Toluene* | 8146.6 | 15.7 | 4215.9 | 158.7 |
| Ethylbenzene* | 1147.4 | nd | 4557.0 | 5.2 |
| Styrene* | 1666.9 | 6.2 | 20012.0 | 38.4 |
| Naphthalene* | 355.5 | nd | 2403.6 | 27.9 |
| m/p Xylene* | 2259.0 | nd | 510.6 | nd |

TABLE 3-continued

Gas Chromatography Data Collected Before and After Microwave Treatment of Emissions Resulting From the Combustion of Unreinforced Circuit Boards

| COMPOUND | SR-8 EMISSIONS (ng) | | SR-9 EMISSIONS (ng) | |
|---|---|---|---|---|
| | A | B | A | B |
| 1,3,5 Trimethylbenzene | 1564.0 | nd | 378.7 | 64.3 |
| 1,2,4 Trimethylbenzene | 904.7 | nd | 171.8 | nd |

A = before microwave off-gas treatment;
B = after microwave off-gas treatment
*Listed in the Clean Air Act (as amended, 1990) as hazardous air pollutants.

The reductions in off-gas constituents is significant and has applications for a variety of off-gas emission sources, regardless of origin. Further, the data is from a combustion treatment chamber having a simple cylindrical shape and a length of approximately 8 inches. By varying the geometry and length of the treatment chamber, is should be possible to increase the volume of introduced off-gases along with enhanced efficiency of the treatment process.

An important feature of the present invention is the use of the hybrid microwave system. As used herein, hybrid refers to the combination of a direct microwave energy bombardment of the waste material along with the radiant infrared heating which occurs through the use of the susceptor materials. For specialty waste applications, it is possible to tune or vary the frequency of the microwave source so as to selectively target a waste constituent. Such targeting is possible in both the primary waste treatment step as well as the treatment of off-gas emissions.

It is known in the art that microwaves can be transmitted substantial distances from a remote magnetron 51 (FIG. 2) via wave guides 53 . As a result, the magnetron can be shielded from reflected microwaves which permits innovative designs for combustion chambers to be constructed. Such abilities are significant in that the present process can be commercially scaled up in ways compatible with conventional off-gas emission source designs.

As set forth in Table 1, there is a significant reduction in the weight of the treated material. Further, as best described in co-pending patent application having Ser. No. 08/605/293 entitled "Methods for Recovering Metals from Waste", and incorporated herein by reference, microwave heating of the electronic, metal-containing waste enables precious metals to be separated and collected from the remaining solid waste material after volatilization. As such, significant amounts of precious and nonprecious metals can be removed from the waste stream and recycled.

The treated residue is more friable than the untreated waste and can be compacted and compressed for waste volume reductions of over 50% of the starting material. Further, the high temperatures of the initial combustion chamber can destroy any bacterial or viral pathogens which may be present on or within the waste. As an additional benefit, the extreme heat transforms material such as medical waste into a decontaminated, sterile product which has been rendered into an unrecognizable, nonhazardous inert waste product. As a result, disposal of the residue of non-radioactive medical waste a the normal sanitary waste stream is possible.

Where significant ceramic and glass materials are present in the waste, the high temperatures will produce a molten glass product without the need for additional additives. Where needed, additional glass formers can be added to the waste to create a vitrified waste product. The vitrified product has been found to immobilize difficult to destroy constituents in a leach-resistant, glass-like matrix while permitting the simultaneous separation and reclamation of precious metals such as gold and silver.

All solid and liquid material microwave treatment processes generate off-gases. The present invention provides for an apparatus and process to further treat off-gases with microwaves to substantially reduce and/or eliminate harmful constituents in the off-gas emissions. However, the off-gas treatment capabilities are not limited to tandem microwave processes. Numerous off-gas emission sources, independent of a microwave waste treatment origin, are capable of being treated with the microwave off-gas process of the present invention. For instance, traditional incinerator off-gases could serve as an off-gas source which is passed through a microwave off-gas unit to destroy additional volatile organic compounds (VOCs). Emission sources as diverse as dry cleaners, university and research fume hood operations, industrial emissions, off-gas from remediation treatments, etc. could be further treated with a microwave off-gas system.

The microwave off-gas treatment system can be customized for particular waste streams. For instance, waste which is contaminated with radioactive materials, including mixed waste, is often vitrified into a solid waste material. The off-gasses from the vitrification process will also contain traces of the radioactive material. By incorporating a ion exchange material specific for the radioactive isotope(s) into the Si—C matrix material or elsewhere in the combustion chamber, the isotopes can be retained within the treatment chamber. As a result, less costly emission systems can be used where mixed waste combustion and/or vitrification is involved.

Finally, it should be noted that the described embodiments and data provided were obtained using modified versions of conventional household microwave units. Such units are useful for small volume waste generators which may treat waste on site as opposed to transporting waste for off-site treatment. Such units are easily transported and can be readily assembled and disassembled.

For commercial waste handling facilities and/or recycling operations, it would be desirable to scale-up the size and output of the equipment so that commercial quantities of waste may be processed. Such modifications are well within the capabilities of one skilled in the art.

Many variations will undoubtedly become apparent to one skilled in the art upon a reading of the above specification with reference to the drawings. Such variations, however, are within the spirit and scope of the invention as defined by the following appended claims.

What is claimed is:

1. A tandem microwave waste disposal system comprising:
   a first combustion chamber in communication with a source of microwaves;
   a second combustion chamber in communication with a source of microwaves, said second combustion chamber having an input region in communication with a first end of a hollow conduit, a second end of said conduit in communication with said first combustion chamber, said second combustion chamber further comprising a susceptor defining a gas-permeable matrix;
   an exhaust port in communication with an output region of said second combustion chamber, wherein evolved combustion off-gases from the first combustion chamber pass through said conduit into an input region of said second combustion chamber whereby said susceptor matrix is maintained at an effective temperature for further treating said off-gases, said treated off-gases exiting through said exhaust port.

2. An off-gas treatment apparatus comprising:
   a combustion chamber having an inlet, an outlet, and a matrix core between said inlet and outlet, said matrix core further comprising a gas permeable susceptor;
   a microwave generator for supplying microwave radiation to the matrix core;
   a pressurized gas stream comprising gaseous organic contaminants, the pressurized gas stream in communication with said inlet;
   wherein, when said matrix core is supplied with microwave radiation, the pressurized gas stream in said core is subject to microwave radiation and elevated temperatures, destroying said organic contaminants.

3. A process of treating waste comprising:
   providing a supply of waste material within a first combustion chamber;
   passing a fluid stream through said first combustion chamber and in proximity to said waste materials;
   exposing said waste material to a combination of microwave energy and radiant energy, said radiant energy supplied by a susceptor in proximity to said waste material;
   directing off-gases from said first combustion chamber to a second combustion chamber;
   radiating said off-gases in said second combustion chamber with microwave energy;
   retaining said off-gases within said second combustion chamber until an effective amount of said off-gases are destroyed, thereby providing treated off-gases;
   venting said treated off-gases.

4. The tandem microwave waste disposal system according to claim 1 wherein said second combustion chamber is maintained at an operating temperature of at least about 1000° C.

5. The disposal system according to claim 1, wherein said first combustion chamber source of microwaves and said second combustion chamber source of microwaves are transmitted from a remote magnetron along a wave-guide.

6. The disposal system according to claim 1 further comprising a pressurized gas stream in communication with said first combustion chamber, said air stream directing said off-gases and air-borne particulates to said second combustion chamber.

7. The process according to claim 3 wherein said waste treating process further comprises detecting said off-gases for a known off-gas constituent value;

comparing said value of said off-gas constituent value to a preset threshold value;

venting said off-gases when said off-gas constituent value is below said threshold level;

redirecting said off-gases constituent through said second combustion chamber when said off-gas constituent value is above a threshold limit;

continuing to pass said off-gases containing said elevated off-gas constituent value through said second combustion chamber until said off-gas constituent value falls below said threshold value.

8. The disposal system according to claim 1 wherein said first chamber is adapted for receiving waste material and exposing said waste material through a combination of direct microwave radiation and radiant heat energy.

9. The disposal system according to claim 1 wherein said second combustion chamber is adapted for receiving off-gases from said first chamber and exposing said off-gases to a combination of direct microwave radiation and radiant heat energy.

10. The disposal system according to claim 1 wherein said first combustion chamber further comprises a treatment zone, said treatment zone being exposed to a substantially inert atmosphere.

11. The process according to claim 3 comprising the additional steps of subjecting said off-gases in said second combustion chamber to a temperature of at least about 1000° C.

12. The disposal system according to claim 1 wherein said second combustion chamber further defines an ion exchange material adapted for removing specific constituents from the off-gases.

13. A microwave unit having an interior, the interior having disposed therein a conduit comprising a susceptor, the conduit having an entrance and an exit;

an inlet defined by the microwave unit and in communication with the interior of the microwave unit;

an outlet defined by the microwave unit and in communication with the conduit exit;

wherein when the conduit is maintained at an elevated temperature by the exposure to microwave radiation, a fluid stream having an organic contaminant is directed towards the inlet, the fluid stream and the contaminant entering the interior of the microwave unit and passing into the entrance of the conduit, the organic contaminant being destroyed as the fluid stream passes through the conduit and before the fluid stream passes through the exit and the outlet of the microwave unit.

14. The microwave unit according to claim 13 wherein the inlet is in direct fluid communication with the conduit.

15. The microwave unit according to claim 13 wherein the conduit comprises a tube partially filled with SiC.

16. The microwave unit according to claim 13 wherein the conduit comprises a straight tube.

17. The microwave unit according to claim 13 wherein an interior of the conduit provides a serpentine pathway for a fluid stream.

* * * * *